United States Patent
Lee et al.

(10) Patent No.: US 10,398,476 B2
(45) Date of Patent: Sep. 3, 2019

(54) IMPLANT ADAPTERS AND RELATED METHODS

(71) Applicant: Medos International Sarl, Le Locle (CH)

(72) Inventors: Kevin Lee, Canton, MA (US); J. Riley Hawkins, Cumberland, RI (US); Sheryl Furlan, Middleboro, MA (US)

(73) Assignee: Medos International Sàrl, Le Locle (CH)

( * ) Notice: Subject to any disclaimer, the term of this patent is extended or adjusted under 35 U.S.C. 154(b) by 122 days.

(21) Appl. No.: 15/377,449

(22) Filed: Dec. 13, 2016

(65) Prior Publication Data

US 2018/0161073 A1    Jun. 14, 2018

(51) Int. Cl.
*A61B 17/70* (2006.01)

(52) U.S. Cl.
CPC ...... *A61B 17/7049* (2013.01); *A61B 17/7034* (2013.01)

(58) Field of Classification Search
CPC .............. A61B 17/7049; A61B 17/705; A61B 17/7052
See application file for complete search history.

(56) References Cited

U.S. PATENT DOCUMENTS

| | | |
|---|---|---|
| 5,261,909 A | 11/1993 | Sutterlin et al. |
| 5,312,405 A | 5/1994 | Korotko et al. |
| 5,569,246 A | 10/1996 | Ojima et al. |
| 5,667,506 A | 9/1997 | Sutterlin |
| 5,716,355 A | 2/1998 | Jackson et al. |
| 5,776,135 A | 7/1998 | Errico et al. |
| 5,885,284 A | 3/1999 | Errico et al. |
| 5,980,523 A | 11/1999 | Jackson |
| 6,050,997 A | 4/2000 | Mullane |
| 6,083,226 A | 7/2000 | Fiz |
| 6,096,039 A | 8/2000 | Stoltenberg et al. |
| 6,238,396 B1 | 5/2001 | Lombardo |
| 6,248,104 B1 | 6/2001 | Chopin et al. |
| 6,280,443 B1 | 8/2001 | Gu et al. |
| 6,309,390 B1 | 10/2001 | Le Couedic et al. |

(Continued)

FOREIGN PATENT DOCUMENTS

| | | |
|---|---|---|
| EP | 1857064 A1 | 11/2007 |
| EP | 2 319 436 A1 | 5/2011 |

(Continued)

OTHER PUBLICATIONS

International Search Report and Written Opinion for Application No. PCT/US2017/031883, dated Aug. 2, 2017. (15 pgs).

(Continued)

*Primary Examiner* — Julianna N Harvey
(74) *Attorney, Agent, or Firm* — Nutter McClennen & Fish LLP

(57) ABSTRACT

Implant adapters and related methods are disclosed herein. Exemplary adapters can allow a single connector to be used interchangeably for rod-to-rod, rod-to-anchor, or anchor-to-anchor attachment. In some embodiments, the adapter can fit within tight spaces, can be adjustable in one or more degrees of freedom, or can be configured to "snap" onto a rod and/or to "drag" against the rod, e.g., for provisional retention and positioning of the connector prior to locking.

31 Claims, 5 Drawing Sheets

(56) References Cited

U.S. PATENT DOCUMENTS

| | | |
|---|---|---|
| 6,328,740 B1 | 12/2001 | Richelsoph |
| 6,402,751 B1 | 6/2002 | Hoeck et al. |
| 6,468,276 B1 | 10/2002 | McKay |
| 6,478,798 B1 | 11/2002 | Howland |
| 6,524,310 B1 | 2/2003 | Lombardo et al. |
| 6,551,318 B1 | 4/2003 | Stahurski |
| 6,554,832 B2 | 4/2003 | Shluzas |
| 6,592,585 B2 | 7/2003 | Lee et al. |
| 6,616,668 B2 | 9/2003 | Altarec et al. |
| 6,676,661 B1 | 1/2004 | Benlloch et al. |
| 6,736,775 B2 | 5/2004 | Phillips |
| 6,736,820 B2 | 5/2004 | Biedermann et al. |
| 6,783,526 B1 | 8/2004 | Lin et al. |
| 6,786,907 B2 | 9/2004 | Lange |
| 6,793,657 B2 | 9/2004 | Lee et al. |
| 6,974,460 B2 | 12/2005 | Carbone et al. |
| 7,029,474 B2 | 4/2006 | Richelsoph et al. |
| 7,104,993 B2 | 9/2006 | Baynham et al. |
| 7,122,036 B2 | 10/2006 | Vanacker |
| 7,163,538 B2 | 1/2007 | Altarac et al. |
| 7,166,108 B2 | 1/2007 | Mazda et al. |
| 7,179,261 B2 | 2/2007 | Sicvol et al. |
| 7,189,236 B2 | 3/2007 | Taylor et al. |
| 7,485,132 B1 | 2/2009 | McBride et al. |
| 7,572,277 B2 | 8/2009 | Roussouly et al. |
| 7,585,314 B2 | 9/2009 | Taylor et al. |
| 7,628,799 B2 | 12/2009 | Richelsoph et al. |
| 7,666,210 B2 | 2/2010 | Franck et al. |
| 7,704,270 B2 | 4/2010 | De Coninck |
| 7,717,938 B2 | 5/2010 | Kim et al. |
| 7,717,940 B2 | 5/2010 | Woods et al. |
| 7,744,632 B2 | 6/2010 | Usher |
| 7,744,634 B2 | 6/2010 | Farris |
| 7,753,940 B2 | 7/2010 | Veldman et al. |
| 7,771,474 B2 | 8/2010 | Cordaro |
| 7,789,897 B2 | 9/2010 | Sanders |
| 7,794,478 B2 | 9/2010 | Nilsson |
| 7,803,174 B2 | 9/2010 | Denis et al. |
| 7,806,912 B2 | 10/2010 | Lawton et al. |
| 7,833,248 B2 | 11/2010 | Markworth et al. |
| 7,837,714 B2 | 11/2010 | Drewry et al. |
| 7,842,071 B2 | 11/2010 | Hawkes |
| 7,901,434 B2 | 3/2011 | Drewry et al. |
| 7,909,854 B2 | 3/2011 | Schwab |
| 7,922,746 B2 | 4/2011 | Miller |
| 7,922,747 B2 | 4/2011 | Kirschman |
| 7,927,355 B2 | 4/2011 | Berrevoets et al. |
| 7,942,901 B2 | 5/2011 | Rezach |
| 7,947,066 B2 | 5/2011 | Tepper et al. |
| 7,959,653 B2 | 6/2011 | Thramann et al. |
| 7,993,371 B2 | 8/2011 | Farris |
| 8,016,862 B2 | 9/2011 | Felix et al. |
| 8,025,679 B2 | 9/2011 | Nichols et al. |
| 8,062,338 B2 | 11/2011 | McBride et al. |
| 8,075,594 B2 | 12/2011 | Purcell |
| 8,080,037 B2 | 12/2011 | Butler et al. |
| 8,097,022 B2 | 1/2012 | Marik |
| 8,109,974 B2 | 2/2012 | Boomer et al. |
| 8,114,133 B2 | 2/2012 | Logan |
| 8,147,519 B2 | 4/2012 | Wilcox |
| 8,152,851 B2 | 4/2012 | Mueller et al. |
| 8,167,908 B2 | 5/2012 | Ely et al. |
| 8,172,879 B2 | 5/2012 | Butler et al. |
| 8,192,467 B2 | 6/2012 | Felix et al. |
| 8,197,515 B2 | 6/2012 | Levy et al. |
| 8,236,028 B2 | 8/2012 | Kalfas et al. |
| 8,241,334 B2 | 8/2012 | Butler et al. |
| 8,246,657 B1 | 8/2012 | Samuel |
| 8,246,665 B2 | 8/2012 | Butler et al. |
| 8,262,700 B2 | 9/2012 | Cho et al. |
| 8,262,701 B2 | 9/2012 | Rathbun et al. |
| 8,292,924 B2 | 10/2012 | Neary et al. |
| 8,298,266 B2 | 10/2012 | Miller |
| 8,298,269 B2 | 10/2012 | Null et al. |
| 8,317,837 B2 | 11/2012 | Rezach et al. |
| 8,337,527 B2 | 12/2012 | Hawkins et al. |
| 8,366,749 B2 | 2/2013 | Sweeney |
| 8,366,750 B2 | 2/2013 | Iott et al. |
| 8,414,616 B2 | 4/2013 | Berrevoets et al. |
| 8,414,617 B2 | 4/2013 | Young et al. |
| 8,419,771 B2 | 4/2013 | Poirier et al. |
| 8,419,773 B2 | 4/2013 | Biedermann et al. |
| 8,430,916 B1 | 4/2013 | Winslow et al. |
| 8,460,342 B2 | 6/2013 | Courtney et al. |
| 8,470,001 B2 | 6/2013 | Trautwein et al. |
| 8,591,550 B2 | 11/2013 | Ludwig et al. |
| 8,617,213 B2 | 12/2013 | Moore et al. |
| 8,628,559 B2 | 1/2014 | Iott et al. |
| 8,641,739 B2 | 2/2014 | McLean et al. |
| 8,657,856 B2 | 2/2014 | Gephart et al. |
| 8,715,323 B2 | 5/2014 | Ballard et al. |
| 8,721,689 B2 | 5/2014 | Butler et al. |
| 8,728,124 B2 | 5/2014 | Miller |
| 8,758,411 B1 | 6/2014 | Rayon et al. |
| 8,771,319 B2 | 7/2014 | Prajapati |
| 8,808,332 B2 | 8/2014 | Iott et al. |
| 8,828,056 B2 | 9/2014 | Buss et al. |
| 8,864,798 B2 | 10/2014 | Weiman et al. |
| 8,864,799 B2 | 10/2014 | Kraus |
| 8,870,923 B2 | 10/2014 | Richelsoph |
| 8,882,803 B2 | 11/2014 | Iott et al. |
| 8,888,777 B2 | 11/2014 | Mullaney |
| 8,888,819 B2 | 11/2014 | Frasier et al. |
| 8,920,471 B2 | 12/2014 | Barrus et al. |
| 8,920,475 B1 | 12/2014 | Ziemek et al. |
| 8,945,186 B2 | 2/2015 | Walker et al. |
| 8,951,289 B2 | 2/2015 | Matityahu |
| 8,998,956 B2 | 4/2015 | George et al. |
| 8,998,961 B1 | 4/2015 | Ziemek et al. |
| 9,005,249 B2 | 4/2015 | Rinner et al. |
| 9,023,087 B2 | 5/2015 | Frankel et al. |
| 9,055,980 B2 | 6/2015 | Biedermann |
| 9,060,815 B1 | 6/2015 | Gustine et al. |
| 9,072,547 B2 | 7/2015 | Harper et al. |
| 9,084,630 B2 | 7/2015 | Mullaney |
| 9,095,380 B2 | 8/2015 | Mir et al. |
| 9,101,400 B2 | 8/2015 | Trieu et al. |
| 9,101,405 B2 | 8/2015 | Dickinson et al. |
| 9,107,703 B2 | 8/2015 | Torres |
| 9,113,961 B2 | 8/2015 | Larroque-Lahitette |
| 9,119,675 B2 | 9/2015 | Lee et al. |
| 9,125,691 B2 | 9/2015 | Gunn |
| 9,131,963 B2 | 9/2015 | Predick |
| 9,131,964 B2 | 9/2015 | Blain et al. |
| 9,149,301 B2 | 10/2015 | Asaad et al. |
| 9,155,565 B2 | 10/2015 | Boomer et al. |
| 9,155,580 B2 | 10/2015 | Cormier et al. |
| 9,186,184 B2 | 11/2015 | Janowski |
| 9,198,696 B1 | 12/2015 | Bannigan et al. |
| 9,204,901 B2 | 12/2015 | Black et al. |
| 9,220,541 B1 | 12/2015 | Dant et al. |
| 9,247,964 B1 | 2/2016 | Shoshtaev |
| 9,265,548 B2 | 2/2016 | Jones et al. |
| 9,271,763 B2 | 3/2016 | Barrus et al. |
| 9,339,307 B2 | 5/2016 | McClintock et al. |
| 9,345,521 B2 | 5/2016 | Ziolo |
| 9,421,041 B2 | 8/2016 | Richelsoph |
| 9,433,445 B2 | 9/2016 | Ramsay et al. |
| 9,451,994 B1 | 9/2016 | Whipple et al. |
| 9,474,554 B2 | 10/2016 | Strnad |
| 9,517,089 B1 | 12/2016 | Casey et al. |
| 9,561,058 B2 | 2/2017 | Lange et al. |
| 9,579,126 B2 | 2/2017 | Zhang et al. |
| 9,615,867 B2 | 4/2017 | Picetti et al. |
| 9,629,663 B2 | 4/2017 | Ludwig et al. |
| 9,649,136 B2 | 5/2017 | George et al. |
| 9,693,808 B2 | 7/2017 | Fauth et al. |
| 9,724,131 B2 | 8/2017 | Bootwala et al. |
| 9,770,269 B1 | 9/2017 | Shoshtaev |
| 2002/0042614 A1 | 4/2002 | Ueyama et al. |
| 2003/0045878 A1 | 3/2003 | Petit et al. |
| 2003/0045879 A1 | 3/2003 | Minfelde et al. |
| 2003/0153914 A1 | 8/2003 | Oribe et al. |
| 2004/0111088 A1 | 6/2004 | Picetti et al. |

(56) References Cited

U.S. PATENT DOCUMENTS

| | | |
|---|---|---|
| 2004/0147929 A1 | 7/2004 | Biedermann et al. |
| 2004/0162558 A1 | 8/2004 | Hegde et al. |
| 2005/0131404 A1 | 6/2005 | Mazda et al. |
| 2005/0171537 A1 | 8/2005 | Mazel et al. |
| 2005/0228378 A1 | 10/2005 | Kalfas et al. |
| 2005/0228382 A1 | 10/2005 | Richelsoph et al. |
| 2006/0039750 A1 | 2/2006 | Thomke et al. |
| 2006/0058789 A1 | 3/2006 | Kim et al. |
| 2006/0064091 A1 | 3/2006 | Ludwig et al. |
| 2006/0079892 A1 | 4/2006 | Roychowdhury et al. |
| 2006/0177263 A1 | 8/2006 | Thomke et al. |
| 2006/0206114 A1 | 9/2006 | Ensign et al. |
| 2006/0229611 A1 | 10/2006 | Avery et al. |
| 2006/0241598 A1 | 10/2006 | Khalili |
| 2006/0282074 A1 | 12/2006 | Renaud et al. |
| 2007/0173825 A1 | 7/2007 | Sharifi-Mehr et al. |
| 2007/0173829 A1 | 7/2007 | Drewry et al. |
| 2007/0233062 A1 | 10/2007 | Berry |
| 2007/0233090 A1 | 10/2007 | Naifeh et al. |
| 2007/0250061 A1 | 10/2007 | Chin et al. |
| 2007/0270805 A1 | 11/2007 | Miller et al. |
| 2007/0270817 A1 | 11/2007 | Rezach |
| 2007/0270818 A1 | 11/2007 | Rezach |
| 2008/0058805 A1 | 3/2008 | Stuart |
| 2008/0082112 A1 | 4/2008 | Lawton et al. |
| 2008/0109039 A1 | 5/2008 | Michielli et al. |
| 2008/0177323 A1 | 7/2008 | Null et al. |
| 2008/0234743 A1 | 9/2008 | Marik |
| 2008/0255617 A1 | 10/2008 | Cho et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0281361 A1 | 11/2008 | Vittur et al. |
| 2009/0036929 A1 | 2/2009 | Reglos et al. |
| 2009/0082812 A1 | 3/2009 | Lewis |
| 2009/0105765 A1 | 4/2009 | Strnad |
| 2009/0157120 A1 | 6/2009 | Marino et al. |
| 2009/0163956 A1 | 6/2009 | Biedermann et al. |
| 2009/0187217 A1* | 7/2009 | Weiman ............ A61B 17/7052 606/257 |
| 2009/0204153 A1 | 8/2009 | Suzuki et al. |
| 2009/0228046 A1 | 9/2009 | Garamszegi |
| 2010/0004693 A1 | 1/2010 | Miller et al. |
| 2010/0010545 A1 | 1/2010 | Park et al. |
| 2010/0094345 A1 | 4/2010 | Saidha et al. |
| 2010/0094346 A1 | 4/2010 | Matityahu |
| 2010/0094349 A1 | 4/2010 | Hammer et al. |
| 2010/0114167 A1 | 5/2010 | Wilcox et al. |
| 2010/0160981 A1 | 6/2010 | Butler et al. |
| 2010/0274286 A1 | 10/2010 | Blain et al. |
| 2010/0280552 A1 | 11/2010 | Lee |
| 2010/0298884 A1 | 11/2010 | Faizan et al. |
| 2010/0324599 A1 | 12/2010 | Montello et al. |
| 2011/0034957 A1 | 2/2011 | Biedermann |
| 2011/0046675 A1 | 2/2011 | Barrus et al. |
| 2011/0066187 A1 | 3/2011 | Fang et al. |
| 2011/0087287 A1 | 4/2011 | Reeder, Jr. et al. |
| 2011/0087288 A1 | 4/2011 | Stevenson et al. |
| 2011/0098748 A1 | 4/2011 | Jangra |
| 2011/0106178 A1 | 5/2011 | Schwab |
| 2011/0112533 A1 | 5/2011 | Venturini et al. |
| 2011/0137345 A1 | 6/2011 | Stoll et al. |
| 2011/0152936 A1 | 6/2011 | Gil et al. |
| 2011/0196425 A1 | 8/2011 | Rezach et al. |
| 2011/0245872 A1 | 10/2011 | Nilsson |
| 2011/0245878 A1 | 10/2011 | Franks et al. |
| 2012/0029571 A1 | 2/2012 | Schwab et al. |
| 2012/0059421 A1 | 3/2012 | Aferzon |
| 2012/0083845 A1 | 4/2012 | Winslow et al. |
| 2012/0095512 A1 | 4/2012 | Nihalani |
| 2012/0130436 A1 | 5/2012 | Haskins et al. |
| 2012/0158064 A1 | 6/2012 | Kroll |
| 2012/0203278 A1 | 8/2012 | Gil et al. |
| 2012/0232593 A1 | 9/2012 | Predick |
| 2012/0259369 A1 | 10/2012 | Hammer |
| 2012/0290013 A1 | 11/2012 | Simonson |
| 2012/0296335 A1 | 11/2012 | Mullaney |
| 2013/0018422 A1 | 1/2013 | Rinner et al. |
| 2013/0030468 A1 | 1/2013 | Le Couedic et al. |
| 2013/0079826 A1 | 3/2013 | Simonson |
| 2013/0085534 A1 | 4/2013 | Hainard et al. |
| 2013/0096617 A1 | 4/2013 | Ballard et al. |
| 2013/0123854 A1 | 5/2013 | Kondrashov et al. |
| 2013/0268004 A1 | 10/2013 | Rathbun |
| 2013/0274807 A1 | 10/2013 | Prajapati |
| 2013/0274808 A1 | 10/2013 | Larroque-Lahitette et al. |
| 2014/0018858 A1 | 1/2014 | Laeng et al. |
| 2014/0066990 A1 | 3/2014 | Akbarnia et al. |
| 2014/0088650 A1 | 3/2014 | Taddia et al. |
| 2014/0114359 A1 | 4/2014 | Hawkes |
| 2014/0135839 A1 | 5/2014 | Frankel et al. |
| 2014/0148856 A1 | 5/2014 | Ibarra et al. |
| 2014/0249581 A1 | 9/2014 | Stachniak |
| 2014/0277146 A1 | 9/2014 | Li et al. |
| 2014/0277160 A1 | 9/2014 | Ziolo |
| 2014/0277163 A1 | 9/2014 | Kretzer et al. |
| 2014/0303674 A1 | 10/2014 | Sasing |
| 2014/0316468 A1 | 10/2014 | Keiser et al. |
| 2014/0336706 A1 | 11/2014 | Garamszegi |
| 2014/0343613 A1 | 11/2014 | Eliasen et al. |
| 2015/0032160 A1 | 1/2015 | Carbone et al. |
| 2015/0057707 A1 | 2/2015 | Barrus et al. |
| 2015/0073479 A1 | 3/2015 | Rinner |
| 2015/0119941 A1 | 4/2015 | Daniels et al. |
| 2015/0190178 A1 | 7/2015 | McCarthy et al. |
| 2015/0196328 A1 | 7/2015 | Hirschl et al. |
| 2015/0223844 A1 | 8/2015 | Leff et al. |
| 2015/0230830 A1 | 8/2015 | Frankel et al. |
| 2015/0313645 A1 | 11/2015 | Hansell |
| 2015/0359568 A1 | 12/2015 | Rezach |
| 2016/0135846 A1 | 5/2016 | Mirda |
| 2016/0143665 A1 | 5/2016 | Biedermann et al. |
| 2016/0166289 A1 | 6/2016 | Alsup et al. |
| 2017/0086885 A1 | 3/2017 | Duncan et al. |
| 2017/0095271 A1 | 4/2017 | Faulhaber |
| 2017/0112540 A1 | 4/2017 | Montello et al. |
| 2017/0119439 A1 | 5/2017 | Ozdil et al. |
| 2017/0128107 A1 | 5/2017 | Alsup et al. |
| 2017/0209182 A1 | 7/2017 | Picetti et al. |
| 2017/0245900 A1 | 8/2017 | Rezach |
| 2017/0281247 A1 | 10/2017 | Murray et al. |
| 2017/0311985 A1 | 11/2017 | Bobbitt et al. |
| 2017/0333087 A1 | 11/2017 | Lee et al. |
| 2017/0333088 A1 | 11/2017 | Lee et al. |
| 2017/0348026 A1 | 12/2017 | Stein et al. |
| 2018/0168694 A1 | 6/2018 | Lee et al. |
| 2018/0228518 A1 | 8/2018 | Carruth et al. |
| 2018/0280062 A1 | 10/2018 | Lee et al. |
| 2018/0280063 A1 | 10/2018 | Lee et al. |

FOREIGN PATENT DOCUMENTS

| | | |
|---|---|---|
| EP | 2730242 A1 | 5/2014 |
| WO | 2005/044119 A2 | 5/2005 |
| WO | 2009/110865 A8 | 12/2009 |
| WO | 2011/004222 A1 | 1/2011 |
| WO | 2011/006155 A1 | 1/2011 |
| WO | 2015/017250 A1 | 2/2015 |

OTHER PUBLICATIONS

Akbarnia, B., et al., "Pediatric Isola® Prebent Rod Placement," (Technique Manual), DePuy Acromed, Oct. 2010; 2 pages.

[No Author Listed] VuePoint II Technique Guide, 2015, NuVasive®, Inc.; 64 pages.

Invitation to Pay Additional Fees for Application No. PCT/US2018/017034, dated May 18, 2018 (18 pages).

International Search Report and Written Opinion for Application No. PCT/US2018/024731, dated Jul. 2, 2018 (17 pages).

* cited by examiner

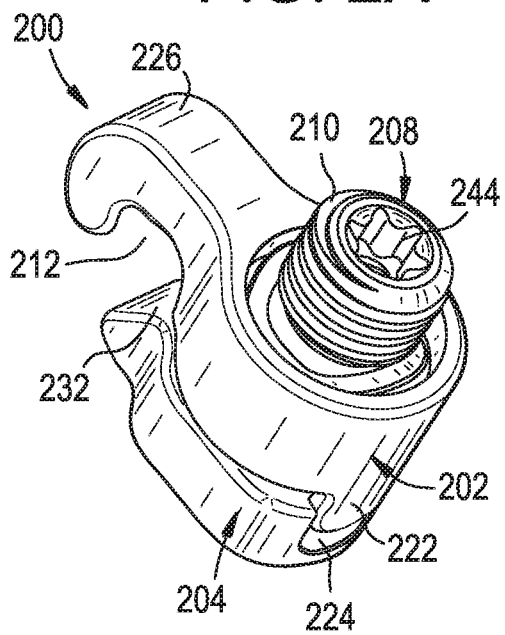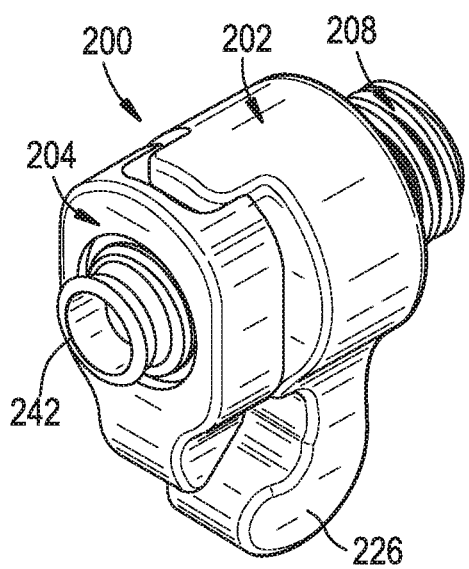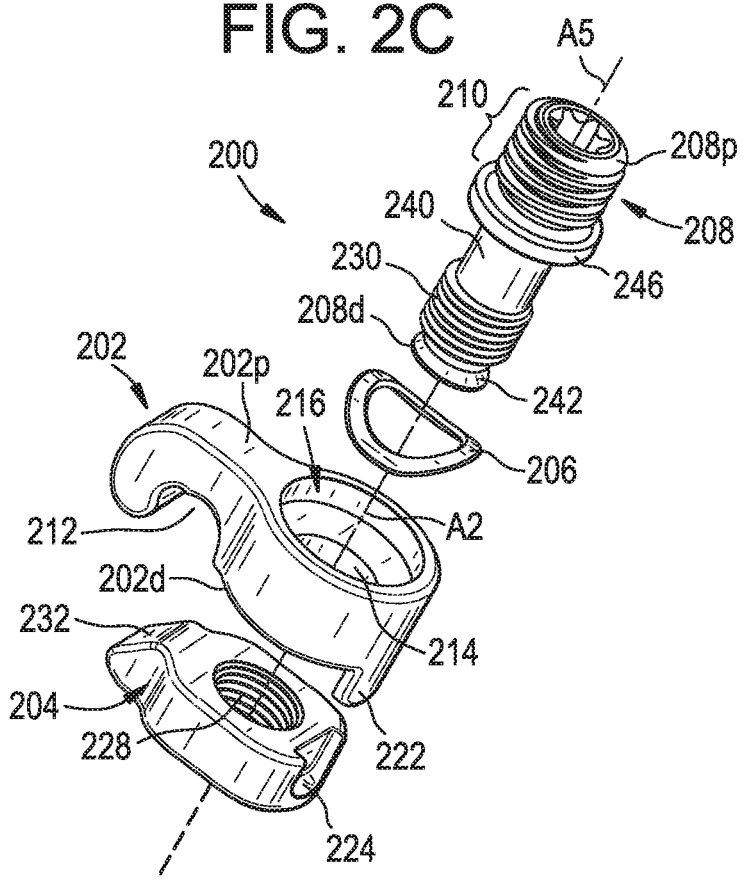

IMPLANT ADAPTERS AND RELATED METHODS

FIELD

Implant adapters and related methods are disclosed herein, e.g., for attaching a connector to a spinal fixation construct in a rod-to-rod or rod-to-anchor arrangement.

BACKGROUND

Implantable constructs can be used in orthopedic surgery to align or fix a desired relationship between two or more bones or bone fragments. In spinal surgery, for example, bone anchors can be used to secure a rod, plate, or other element to one or more vertebrae to rigidly or dynamically stabilize the spine. Exemplary bone anchors include screws, hooks, bolts, wires, and the like.

Connectors are often used to reinforce the construct and provide additional torsional stability. For example, transconnectors (which may also be known as cross-connectors or cross-links) can be used in a posterior fixation construct to attach a first portion of the construct disposed on one side of the spinal midline to a second portion of the construct disposed on the opposite side of the midline. While this arrangement is typical, connectors can also be used with lateral or anterior fixation constructs, and need not necessarily cross the midline of the spine. For example, the connector can be oriented substantially parallel to the midline.

Connectors are usually attached to the construct at a bone anchor connection or at a rod connection. Most connectors are designed either for rod-to-rod attachment or anchor-to-anchor attachment, and do not allow for rod-to-anchor connections. A rod-to-anchor connection can be desirable in some instances, for example when the spinal anatomy does not allow placement of a bone anchor on one side and there is not enough space on the contralateral side for the connector to attach to a rod.

While current connectors have proven effective, it can be difficult to attach the connector in tight spaces, or to maintain the connector in a desired position and orientation during assembly. Existing connectors may also lack modularity or adjustability, reducing options for the surgeon or increasing the number of parts that must be made available for the surgery.

SUMMARY

Implant adapters and related methods are disclosed herein. Exemplary adapters can allow a single connector to be used interchangeably for rod-to-rod, rod-to-anchor, or anchor-to-anchor attachment. In some embodiments, the adapter can fit within tight spaces, can be adjustable in one or more degrees of freedom, or can be configured to "snap" onto a rod and/or to "drag" against the rod, e.g., for provisional retention and positioning of the connector prior to locking.

In some embodiments, an implant adapter includes a body having proximal and distal ends that define a body axis extending therebetween, the body including a rod-receiving channel and an opening; a locking element received through the opening of the body; a clamping arm coupled to the locking element; and a bias element that biases the clamping arm towards the channel of the body; wherein the adapter has a locked configuration in which the clamping arm is configured to clamp a rod against the channel of the body to prevent movement between the rod and the adapter; and wherein the adapter has an unlocked configuration in which the clamping arm can: (1) translate axially relative to the body along the body axis, (2) translate laterally relative to the body in a direction perpendicular to the body axis, and (3) rotate relative to the body about an axis perpendicular to the body axis.

The clamping arm can be constrained from rotating relative to the body about the body axis and any axis parallel to the body axis in both the locked and unlocked configurations. One of the body and the clamping arm can include a male key that is received within a female keyway formed in the other of the body and the clamping arm. The channel can be formed in a hook projecting radially outward from the body, the hook having a height parallel to a rod axis of the channel that is less than half a diameter of the channel. The channel can have a radius of curvature that varies along the perimeter of the channel. The opening of the body can be enlarged relative to a portion of the locking element received therein. The opening can be cylindrical and can have a diameter greater than a diameter of a corresponding cylindrical portion of the locking element received within the opening. The opening can be elongated and can include a major dimension that is greater than a diameter of a corresponding cylindrical portion of the locking element received within the opening and a minor dimension that is substantially equal to the diameter of the corresponding cylindrical portion of the locking element. The major dimension can be perpendicular to a rod axis of the channel and perpendicular to the body axis. The locking element can include a screw that is threaded into a threaded recess formed in the clamping arm. The locking element can include a shoulder projecting radially outward therefrom. The bias element can be disposed between the body and the shoulder of the locking element. The bias element can include a wave spring. The bias element can include a compression spring, a Belleville washer, or a washer with tabs. The shoulder can define a spherical distal-facing surface positioned opposite to a spherical proximal-facing surface of the body. The locking element can include a mating feature configured to attach the adapter to a link of a connector. The mating feature can include a proximal head of the locking element having an externally-threaded surface. The clamping arm and the body can define an aperture therebetween through which a rod can be passed to insert the rod into the channel of the body. The aperture can be configured to expand as a rod is passed therethrough and to contract once the rod is positioned in the channel such that the adapter, in the unlocked configuration, is configured to snap onto and retain the rod within the channel. In the unlocked configuration, the bias element can urge the clamping arm against a rod received in the channel to apply a drag force to the rod.

In some embodiments, an implant adapter includes a body having proximal and distal ends that define a body axis extending therebetween, the body including a rod-receiving channel and an opening; a locking element received through the opening of the body; a clamping arm coupled to the locking element; and a bias element that biases the clamping arm towards the channel of the body; wherein the adapter has a locked configuration in which the clamping arm is configured to clamp a rod against the channel of the body to prevent movement between the rod and the adapter; and wherein the adapter has an unlocked configuration in which the locking element can: (1) translate axially relative to the body along the body axis, (2) translate laterally relative to the body in a direction perpendicular to the body axis, (3)

rotate relative to the body about an axis perpendicular to the body axis, and (4) rotate relative to the body about the body axis.

In some embodiments, a spinal fixation method includes passing an elongate rod through an aperture defined between a clamping arm and a body of an adapter, the body having proximal and distal ends that define a body axis extending therebetween, wherein passing the rod through the aperture comprises (i) translating the clamping arm laterally relative to the body in a direction perpendicular to the body axis, and (ii) rotating the clamping arm relative to the body about an axis perpendicular to the body axis; biasing the clamping arm towards the body to snap the adapter onto the rod and to exert a drag force on the rod; actuating a locking element of the adapter to prevent relative movement between the adapter and the rod and between the clamping arm and the body; and attaching a connector to a mating feature of the adapter.

The connector can include opposed first and second ends. Attaching the connector can include attaching the first end of the connector to the mating feature of the adapter. The method can include attaching the second end of the connector to at least one of a bone anchor and a rod. Passing the rod through the aperture can include (iii) translating the clamping arm relative to the body along the body axis. The clamping arm can be constrained from rotating relative to the body about the body axis and any axis parallel to the body axis before and after the locking element is actuated. Actuating the locking element can include threading the locking element into the clamping arm to clamp the rod between the clamping arm and the body. The method can include pivoting the locking element within an opening formed in the body. The method can include pivoting a spherical distal-facing surface of the locking element relative to an opposed spherical proximal-facing surface of the body. The method can include compressing the bias element between the spherical surface of the locking element and the spherical surface of the body. The body can include a channel having a plurality of regions each having a different radius of curvature. The method can include positioning the rod in one of the plurality of regions of the channel. Attaching the connector can include positioning a central axis of the connector at an oblique angle relative to (i) a midline of a patient's spine and (ii) first and second rods positioned on opposite sides of the midline.

BRIEF DESCRIPTION OF THE DRAWINGS

FIG. 2A is a perspective view of the adapter of FIGS. 1B-1C;

FIG. 2B is another perspective view of the adapter of FIG. 2A;

FIG. 2C is an exploded perspective view of the adapter of FIG. 2A;

DETAILED DESCRIPTION

Implant adapters and related methods are disclosed herein. Exemplary adapters can allow a single connector to be used interchangeably for rod-to-rod, rod-to-anchor, or anchor-to-anchor attachment. In some embodiments, the adapter can fit within tight spaces, can be adjustable in one or more degrees of freedom, or can be configured to "snap" onto a rod and/or to "drag" against the rod, e.g., for provisional retention and positioning of the connector prior to locking.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1A:
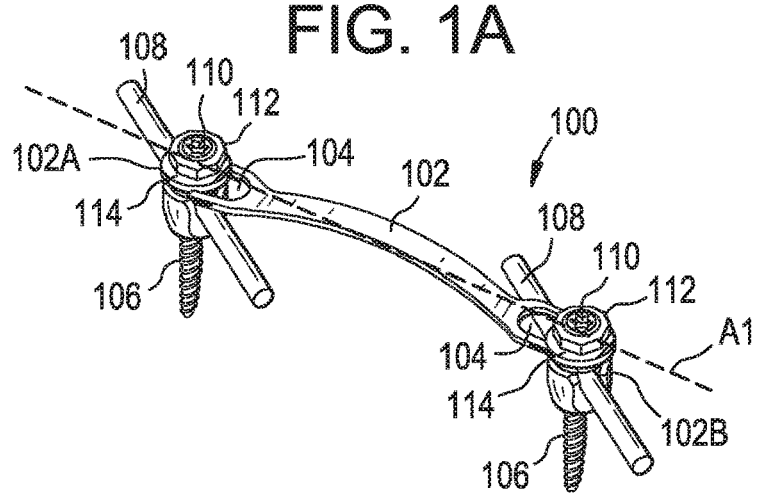
FIG. 1A is a perspective view of a connector attached to a construct in an anchor-to-anchor arrangement.
Figure 1B:
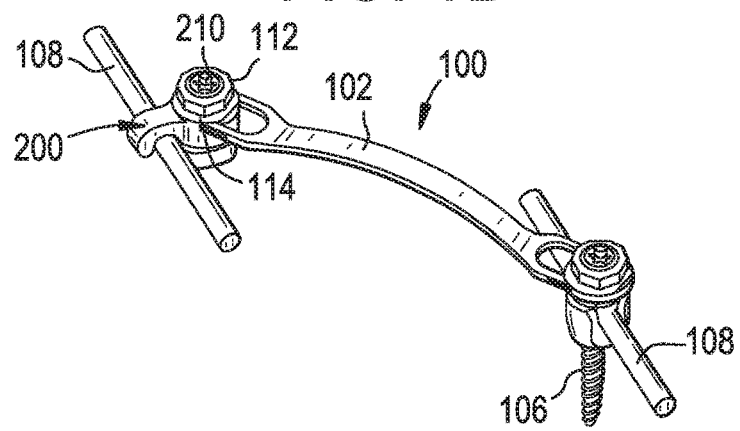
FIG. 1B is a perspective view of the connector of FIG. 1A attached to a construct in a rod-to-anchor arrangement using an adapter.
Figure 1C:
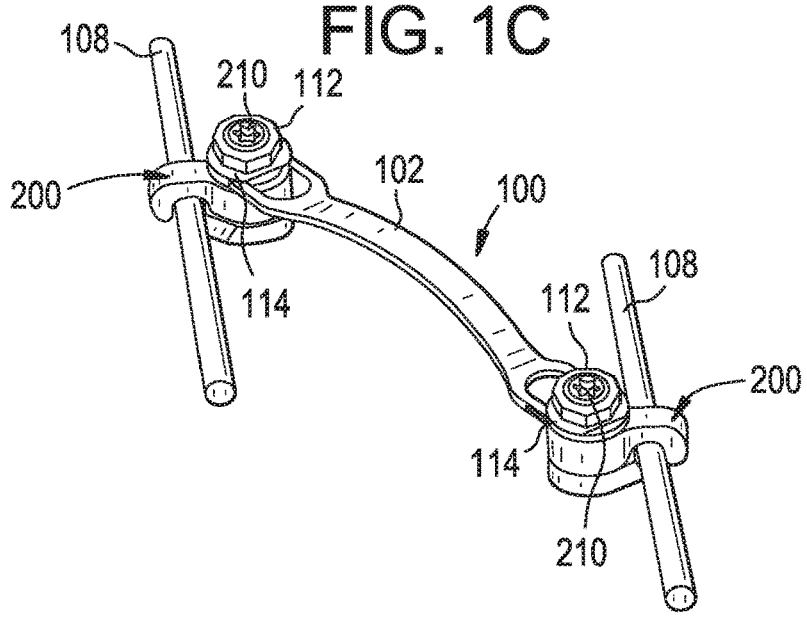
FIG. 1C is a perspective view of the connector of FIG. 1A attached to a construct in a rod-to-rod arrangement using two adapters.

FIGS. 1A-1C illustrate an exemplary embodiment of a connector 100 that can be used, for example, to connect first and second portions of an implanted construct. The connector 100 can include a connecting bar or link 102 configured to span between the first and second portions of the construct. The link 102 can include first and second opposed ends 102A, 102B that define a central longitudinal axis A1 therebetween. The link 102 can be curved along the axis A1 as shown to provide clearance for anatomical structures or other implants. The link 102 can define one or more attachment points for attaching the link to an implanted construct. For example, the link 102 can include elongated slots or openings 104 at each end to allow the link to be attached to an implant mating feature.

The connector 100 can be used in an anchor-to-anchor arrangement, as shown in FIG. 1A, in which the connector is attached to first and second bone anchors 106. The bone anchors 106 can be implanted on opposite sides of a midline of a patient's spine. The bone anchors 106 can be used to secure first and second respective spinal rods 108 to the spine. Each bone anchor 106 can include a threaded post 110, e.g., defined by part of the bone anchor's set screw or closure mechanism, that is received through an opening 104 in the link 102 and secured thereto by a locking nut 112. A sliding washer 114 can be positioned between the locking nut 112 and the link 102 to further secure the connection.

The connector 100 can also be used in a rod-to-anchor arrangement, for example by attaching an adapter 200 to one end of the link 102 as shown in FIG. 1B, or in a rod-to-rod arrangement, for example by attaching an adapter 200 to both ends of the link 102 as shown in FIG. 1C. The adapter 200 can include a mating feature 210 similar or identical to that of the bone anchor 106 to allow the link 102, washer 114, and locking nut 112 to be used interchangeably to connect to a rod 108 or to connect to a bone anchor 106.

Exemplary bone anchors and exemplary connectors, including links, sliding washers, and locking nuts, are described in U.S. Pat. No. 8,591,550 issued on Nov. 26, 2013 and entitled ROD ATTACHMENT FOR HEAD TO HEAD CONNECTOR, the entirety of which is hereby incorporated by reference for all purposes. The connectors 100 described herein can include any of the features described in the above reference.

An exemplary adapter 200 is shown in greater detail in FIGS. 2A-2F. As shown, the adapter 200 can include a body 202, a clamping foot or arm 204, a bias element or spring 206, a locking element 208, and a mating feature 210 for attaching the adapter to a cross bar or link 102 of a connector 100. The body 202 can define a recess or channel 212 sized to receive a spinal fixation element, such as a spinal rod, therein. The bias element 206 can bias the clamping arm 204 towards the channel 212 to allow the adapter 200 to "snap" onto the rod and/or to "drag" against the rod, e.g., for provisional retention and positioning of the adapter prior to locking. The locking element 208 can be actuated to clamp the rod between the body 202 and the clamping arm 204 to secure the rod to the adapter 200 and lock one or more degrees of freedom between the adapter and the rod. The locking element 208 can be received in an oversized opening 214 formed in the body 202 to allow the locking element and the clamping arm 204 to translate and pivot relative to the body.

The body 202 can include proximal and distal ends 202*p*, 202*d* that define a central proximal-distal body axis A2 extending therebetween. A recess 216 can be formed in the proximal-facing surface of the body 202 and can be defined by a sidewall 218 and a floor 220. An opening 214 can be formed in the body 202 and can extend from the floor 220 of the recess 216 to the distal-facing surface of the body. The locking element 208 can be received through the recess 216 and through the opening 214, either or both of which can be configured to allow movement of the locking element relative to the body 202 with multiple degrees of freedom.

Figure 2D:
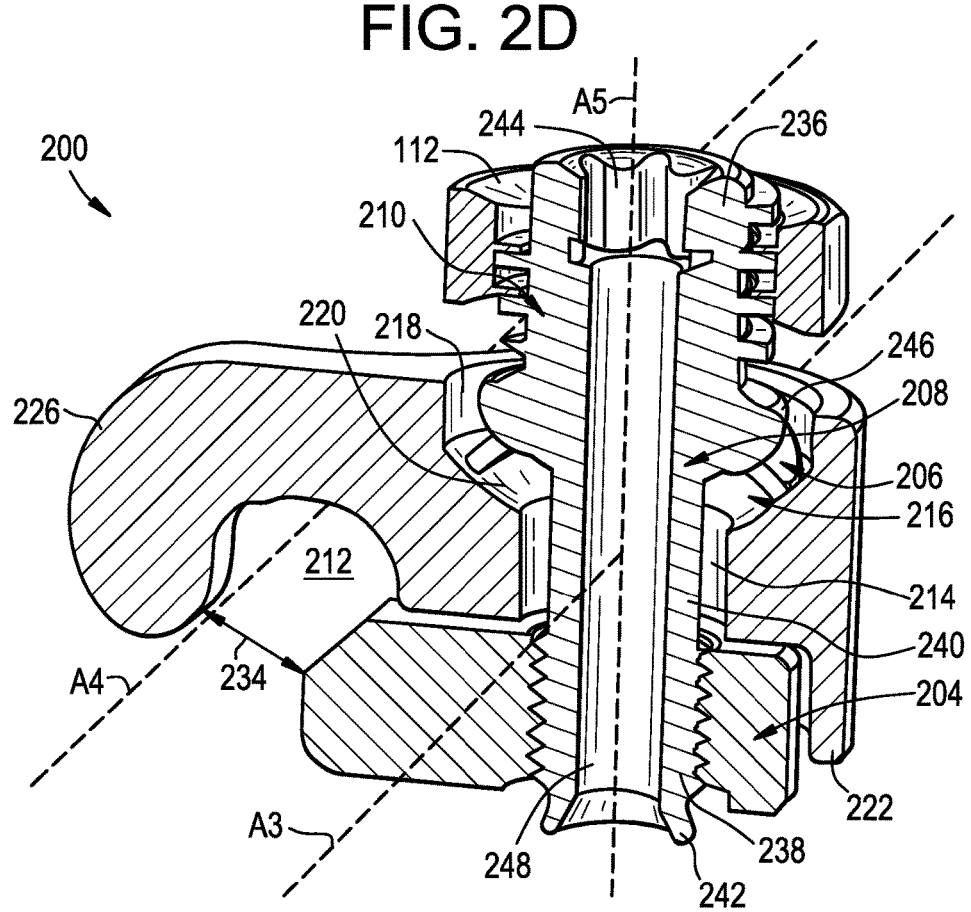
FIG. 2D is a sectional view of the adapter of FIG. 2A, shown with a locking nut.
Figure 2E:
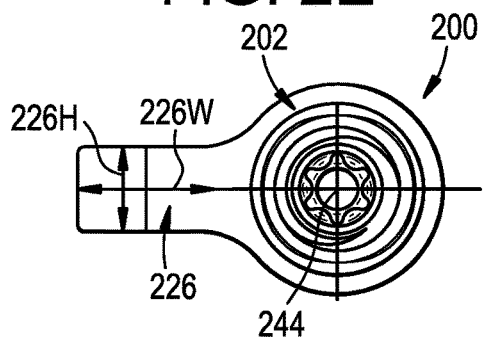
FIG. 2E is a top view of the adapter of FIG. 2A.

The adapter 200 can be configured to allow (1) translational movement of the locking element 208 relative to the body 202 along the proximal-distal axis A2 of the body, (2) rotational movement of the locking element 208 relative to the body 202 about the proximal-distal axis A2 of the body, (3) translational movement of the locking element 208 relative to the body 202 in a direction perpendicular to the proximal-distal axis A2 of the body, and (4) rotational movement of the locking element 208 relative to the body 202 about one or more pivot axes, e.g., a pivot axis A3 as shown in FIG. 2D, that are perpendicular to the proximal-distal axis A2 of the body.

For example, the floor 220 of the recess 216 can define a concave spherical surface to allow polyaxial movement of the locking element 208 relative to the body 202. As another example, the opening 214 can be oversized relative to the portion of the locking element 208 received therethrough to allow the locking element to translate laterally and/or pivot within the opening.

The opening 214 can be cylindrical and can have a diameter that is greater than the diameter of the portion of the locking element 208 received within the opening. Such an arrangement can allow the locking element 208 to translate relative to the body 202 in all directions perpendicular to the axis A2 and to pivot relative to the body about one or more pivot axes, e.g., a pivot axis A3 as shown, that are perpendicular to the proximal-distal axis A2 of the body.

The opening 214 can be elongated and can include at least one dimension that is greater than the diameter of the portion of the locking element 208 received within the opening. For example, the opening 214 can have a major dimension and a minor dimension in a plane normal to the axis A2. The major dimension can be greater than the diameter of the portion of the locking element 208 received within the opening 214 and the minor dimension can be equal to or only slightly greater than said portion such that lateral translation of the locking element relative to the body 202 is substantially limited to being along the major dimension. The major dimension can be perpendicular to a rod axis A4 of the adapter 200, can be parallel to the rod axis A4, or can be obliquely angled with respect to the rod axis A4.

The opening 214 can be oversized to varying degrees relative to the portion of the locking element 208 received therethrough. The diameter or the major dimension of the opening 214 can be at least 10% greater, at least 20% greater, and/or at least 30% greater than the diameter of the portion of the locking element 208 received therethrough. The diameter or the major dimension of the opening 214 can be 10% to 50% greater, 20% to 40% greater, and/or 25% to 35% greater than the diameter of the portion of the locking element 208 received therethrough. The diameter or the major dimension of the opening 214 can be 30% greater than the diameter of the portion of the locking element 208 received therethrough.

The body 202 can include features that cooperate with the clamping arm 204 to limit movement of the clamping arm relative to the body. For example, the body 202 can be configured to limit or prevent rotation of the clamping arm 204 relative to the body about the axis A2. The body 202 can include a distally-projecting key 222 that is received in a corresponding keyway 224 formed in the clamping arm 204 to limit or prevent such rotation. Alternatively, or in addition, a male key can formed on the clamping arm 204 and can be received within a female keyway formed in the body 202. The keyway 224 can be open on at least one side or can be enlarged relative to the key 222 in at least one direction to allow the clamping arm 204 to translate relative to the body 202 perpendicular to the axis A2 and to pivot relative to the body about one or more pivot axes, e.g., the pivot axis A3 as shown, that are perpendicular to the axis A2.

The body 202 can include a cantilevered hook or wing portion 226 that defines the rod-receiving channel 212. A rod disposed in the rod-receiving channel 212 can have a central longitudinal rod axis A4. The axis A4 can be perpendicular to the axis A2 as shown, or can be parallel or obliquely angled with respect to the axis A2. The wing portion 226 can extend radially-outward from a main portion of the body 202. The main portion of the body can be cylindrical or substantially cylindrical as shown. The wing portion 226 can have a width 226W and a height 226H. A ratio of the width 226W to the diameter of the rod-receiving channel 212 (or of a rod disposed therein) can be less than about 1.5:1, less than about 2:1, and/or less than about 3:1. A ratio of the height 226H to the diameter of the rod-receiving channel 212 (or of a rod disposed therein) can be less than about 0.5:1, less than about 1:1, and/or less than about 2:1. In some embodiments, the height 226H can be less than about 5 mm, less than about 4 mm, and/or less than about 3 mm. Accordingly, the wing portion 226 can have a low profile in the height dimension, which can advantageously facilitate use of the adapter 200 in tight spaces, e.g., a space between bone anchors implanted in adjacent vertebral levels, including closely-spaced cervical vertebrae. The rod-receiving channel 212 can be open in a distal direction such that a rod can be inserted into the recess by moving the adapter 200 distally with respect to the rod. In other embodiments, the rod-receiving channel 212 can be open in a proximal direction, e.g., by flipping the wing portion 226 and forming it such that it extends from a distal portion of the body 202, or open in a lateral direction.

Figure 2F:
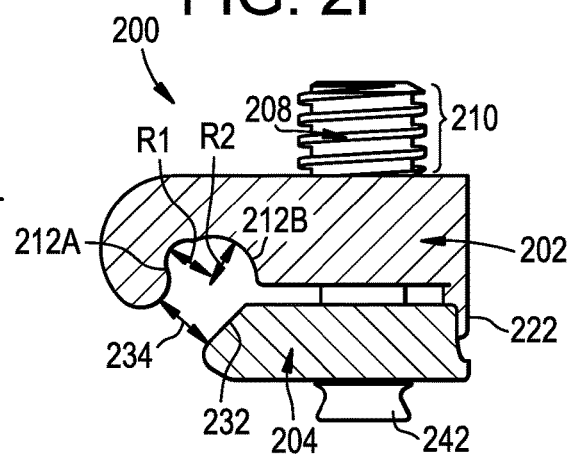
FIG. 2F is a side view of the adapter of FIG. 2A.

As shown in FIG. 2F, the radius of curvature of the rod channel 212 can vary along the perimeter of the channel. For example, the rod channel 212 can include a first portion 212A having a radius of curvature R1 and a second portion 212B having a radius of curvature R2. R1 can be different from R2. While two sections having different curvatures are shown, it will be appreciated that the channel 212 can have any number of sections, e.g., one, two, three, four, five, etc. Including channel sections with different radii can allow the same channel to be used with rods having different diameters. In the illustrated example, a rod having a radius equal or substantially equal to the radius R1 can be urged into the first portion 212A of the channel 212 to secure the rod to the adapter 200, or another rod having a diameter equal or substantially equal to the radius R2 can be urged into the second portion 212B of the channel 212 to secure the rod to the adapter 200.

Referring again to FIG. 2C, the clamping arm 204 can include proximal and distal surfaces and can define an opening 228 that extends between the proximal and distal surfaces. While the illustrated opening 228 extends completely through the clamping arm 204, in other embodiments the opening can be a blind bore formed in the proximal surface of the clamping arm. The opening 228 can be threaded to engage corresponding threads 230 formed on the locking element 208. The clamping arm 204 can include a rod-contacting surface 232. The rod-contacting surface 232 can extend at an oblique angle from proximal and distal surfaces of the clamping arm 204. The rod-contacting surface 232 can be a planar ramped surface as shown, or can have a convex or concave curvature. For example, the rod-contacting surface 232 can be concave and can have a radius of curvature that corresponds to that of a rod with which the adapter 200 is to be used. The rod-contacting surface 232 can bear against a rod disposed in the rod-receiving channel 212 of the body 202 to snap onto the rod, drag against the rod, and/or lock the rod within the channel, as described further below. As noted above, the clamping arm 204 can cooperate with the body 202 to limit movement of the clamping arm relative to the body. For example, the clamping arm 204 can include a keyway 224 that receives the key 222 of the body 202 to limit or prevent rotation of the clamping arm relative to the body about the axis A2.

The body 202 and the clamping arm 204 can define an aperture 234 therebetween sized and/or shaped according to the rod to which the adapter 200 is to be coupled. For example, when the adapter 200 is in an unloaded configuration, an opening dimension of the aperture 234 can be substantially equal to a diameter of the rod. Alternatively, the opening dimension of the aperture 234 can be slightly less than the diameter of the rod to allow for a snap-fit engagement that provides retention and tactile and/or audible feedback to the surgeon when the adapter 200 "snaps" onto the rod. As another alternative, the opening dimension of the aperture 234 can be slightly greater than that of the rod, with any play being taken up by the clamping action when the locking element 208 is tightened. The adapter 200 can thus be configured to couple to rods or other fixation elements of various sizes or shapes. In some embodiments, a plurality of adapters 200, each having apertures 234 with different sizes or shapes, can be provided as part of a kit to allow for selection of an adapter 200 sized and shaped appropriately for a particular application.

The bias element 206 can be disposed between the body 202 and the locking element 208 and can be configured to bias the clamping arm 204 towards the channel 212 formed in the body. Accordingly, the opening dimension of the aperture 234 can increase as the clamping arm 204 and the body 202 are spread apart against the bias of the bias element 206 when a rod is inserted into the adapter 200. Once the rod clears the leading end of the wing portion 226 of the body 202 and is fully-disposed within the channel 212, the bias element 206 can cause the clamping arm 204 and the body to move towards each other to reduce the opening dimension of the aperture 234, thereby providing a "snap fit" engagement with tactile and/or audible feedback to the user. The bias force can cause the clamping arm 204 to contact and apply friction to the rod, even before the locking element 208 is tightened. This can allow the adapter 200 to "drag" against the rod, which can limit or prevent translation and rotation of the adapter relative to the rod about the rod axis A4 unless specifically intended by a user, e.g., until a user applies a force to the adapter 200 sufficient to overcome the frictional engagement between the adapter and the rod.

In the illustrated embodiment, the bias element is a wave spring or washer 206. The wave spring 206 can be bent in one or more planes and can include a central opening through which the locking element 208 can be received. The wave spring 206 can be formed from a flexible and resilient material configured to deform to the shape of a flat washer when an external force (e.g., the force of the rod being introduced through the aperture 234 or the force of the locking element 208 being tightened to the clamping arm 204) is applied and to spring back to the wave shape shown in FIG. 2C when the external force is removed. While a wave spring 206 is shown, it will be appreciated that other bias elements can be used instead or in addition, such as coil springs, leaf springs, a compressible and resilient O-ring, a disc spring or Belleville washer, a washer with tabs (e.g., a plastic washer with tabs), a compression spring, etc.

While any of a variety of locking elements can be used, in the illustrated embodiment, the locking element is a locking screw 208. The locking screw 208 can include a proximal end 208p and a distal end 208d that define a central longitudinal axis A5 extending therebetween. While the central axis A5 of the locking screw 208 is shown as being collinear with the proximal-distal axis A2 of the body 204, it will be appreciated that relative movement between the locking screw and the body can allow the axes A2, A5 to be laterally offset and/or obliquely angled with respect to one another. The locking screw 208 can include a proximal head portion 236 and a distal shank portion 238. The shank 238 of the locking screw 208 can be threaded along its entire length or along only a portion of its length. In some embodiments, a distal section 230 of the shank 238 can be threaded to engage the threaded opening 228 of the clamping arm 204 and an intermediate section 240 proximal to the distal section can be left unthreaded to allow the locking screw 208 to freely rotate, translate, and pivot within the opening 214 of the body 202 until the locking screw is tightened. The intermediate section 240 of the locking screw 208 can have a diameter that is less than the diameter or major dimension of the opening 214 in the body 202 to allow such movement.

As noted above, at least a portion of the opening 228 formed in the clamping arm 204 can be threaded and can be configured to threadably engage the distal threaded portion 230 of the shank 238. Accordingly, rotation of the locking screw 208 relative to the clamping arm 204 in a first direction can be effective to draw the body 202 and the clamping arm 204 together and relative rotation in a second, opposite direction can be effective to allow the body and the clamping arm to move apart (e.g., under the bias of the bias element 206). The locking screw 208 can be configured to prevent disassembly of the adapter 200 once assembled. For example, the distal end 208d of the locking screw 208 can be swaged to form a flared portion 242 after the clamping arm 204 is threaded onto the locking screw to prevent the locking screw from being completely unthreaded from the clamping arm.

The head portion 236 of the screw 208 can include a driving interface (e.g., a female recess 244 in which a screwdriver or other instrument can be received) to facilitate rotation and tightening or loosening of the locking screw 208. The head portion 236 of the screw 208 can define the mating feature 210 for coupling the adapter 200 to the link 102 shown in FIGS. 1A-1C. For example, as shown, the head 236 can define a post sized to fit through an opening 104 formed in the link 102. An exterior surface of the head 236 can be threaded to receive a locking nut 112 to secure the link 102 to the adapter 200, e.g., by squeezing the link 102 and/or a washer 114 coupled thereto between a distal surface of the nut 112 and a proximal surface of the body 202. While the mating feature 210 is formed on the locking screw 208 in the illustrated embodiment, in other embodiments it can be formed elsewhere on the adapter 200. For example, the body 202 or the clamping arm 204 can include a threaded post or other mating feature for attaching to the link 102. As another example, the link 102 can be formed integrally as a single monolithic unit with either the body 202 or the clamping arm 204. While a threaded mating feature 210 is shown, other mating features can be used instead or in addition. For example, the locking screw 208 can be swaged to the link 102 or can be mated to the link using a fastener such as a cap that slides laterally onto the locking screw to retain the link.

The locking screw 208 can include a generally annular protrusion or shoulder 246 extending radially outward therefrom. The shoulder 246 can include a distal-facing surface that is opposed to the floor 220 of the recess 216 formed in the body 202. The bias element 206 can be received within the recess 216 formed in the body 202 and can bear against the distal-facing surface of the shoulder 246 and the proximal-facing floor 220 of the recess. The distal-facing floor 220 of the shoulder 246 can have a geometry that corresponds to the geometry of the floor 220 of the recess 216. For example, the shoulder 246 can define a spherical distal-facing surface with a radius of curvature that is equal or substantially equal to the radius of curvature of the spherical floor 220 of the recess 216. This can allow the locking element 208 to move polyaxially with respect to the body 202. In other words, the central longitudinal axis A5 of the locking element 208 can be positioned at any of a variety of angles with respect to the central-longitudinal axis A2 of the body 202 within a cone of angulation. In an exemplary embodiment, the locking element 208 can be pivoted up to 15 degrees in any direction with respect to the body 202. The bias element 206 can be configured to conform to the opposed spherical surfaces of the floor 220 and the shoulder 246 when the locking element 208 is tightened to lock the locking element to the body 202 at a desired angle. The locking element 208 can be cannulated or can define a central passage 248, e.g., to allow the adapter 200 to be inserted over a guidewire or other insertion guide.

In use, the adapter 200 can be positioned in an unloaded configuration in which the locking element 208 is not tightened to the clamping arm 204 and no rod is inserted into the channel 212 of the body 202. In the unloaded configuration, the bias element 206 can bias the locking element 208 and the clamping arm 204 coupled thereto proximally relative to the body 202, closing the aperture 234 defined between the clamping arm and the channel 212 to a minimum distance.

The adapter 200 can also be positioned in an unlocked configuration in which the locking element 208 is not tightened to the clamping arm 204 and a rod is received within the channel 212 of the body 202. The rod can have a diameter that is greater than the minimum distance of the aperture 234 such that, as the rod is inserted into the channel 212, the rod moves the clamping arm 204 away from the body 202. This movement can result from (1) the locking element 208 and the clamping arm 204 translating distally relative to the body 202 along the axis A2; (2) the locking element 208 and the clamping arm 204 translating laterally relative to the body 202, in a direction perpendicular to the axis A2; and/or (3) the locking element 208 and the clamping arm 204 rotating relative to the body 202 about an axis that extends perpendicular to the axis A2, e.g., the illustrated axis A3 that is both perpendicular to the axis A2 and parallel to the rod axis A4. The bias element 206 can provide resistance to all three of these motion components, such that once the rod clears the aperture 234 and is seated in the recess 212, the clamping arm 204 springs back to close the aperture slightly and provide a snapping effect as the rod is captured. The bias element 206 can urge the locking element 208 and the clamping arm 204 towards the rod, e.g., proximally relative to the body 202, to exert a drag force on the rod. Accordingly, in the unlocked configuration, the adapter 200 can be configured to snap onto and drag against the rod.

In the unlocked configuration, the rod can still be translated relative to the adapter 200 along the rod axis A4 or rotated relative to the adapter about the rod axis A4 when sufficient force is applied to overcome the drag force. Typically, such force would only be produced when the user specifically intends to adjust the position or orientation of the adapter 200 with respect to the rod. This can allow the adapter 200 to be placed in a provisional position or orientation with respect to the rod and to remain in place without tightening the locking element 208. The freedom of movement between the clamping arm 204 and the body 202 described above can advantageously allow the adapter 200 to be used with rods of varying diameter and to produce a snap and drag effect regardless of the rod diameter. In some embodiments, the adapter 200 can apply a snap and drag effect to rods having a diameter in the range of about 2 mm to about 8 mm, in the range of about 3 mm to about 6.5 mm, and/or in the range of about 5 mm to about 6 mm.

The adapter 200 can also be positioned in a locked configuration in which the locking element 208 is tightened to the clamping arm 204. In particular, the locking screw 208 can be rotated within the clamping arm 204 to cause the locking element to translate distally within the clamping arm and to squeeze the body 202 and the clamping arm 204 towards one another. As the locking screw 208 is tightened, the bias element 206 can be compressed between the locking element and the body 202. Also as the locking screw 208 is tightened, the clamping arm 204 can clamp down on a rod received within the channel 212 of the body. In the case of a channel 212 having varying radii of curvature, this clamping force can direct the rod into the portion of the channel having a radius equal to or most-closely matching that of the rod. In the locked configuration, the rod can be secured to the adapter 200 in all degrees of freedom such that the rod cannot translate or rotate relative to the adapter.

Figure 3A:
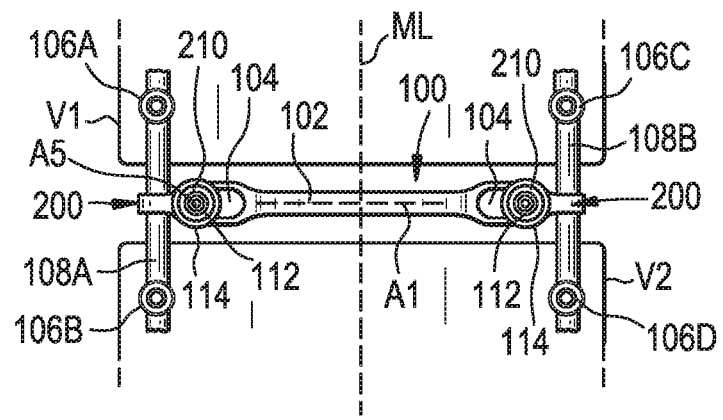
FIG. 3A is a top view of the connector and adapters of FIG. 1C attached to a spine in a perpendicular rod-to-rod arrangement.

In use, the connector 100 can be used to connect first and second portions of a fixation construct. For example, as shown in FIG. 3A, a fixation construct can include a first portion attached to the posterior aspect of a patient's spine on one side of the midline ML and a second portion attached to the posterior aspect of the patient's spine on the opposite side of the midline. The first portion can include a first elongate spinal rod 108A that extends substantially parallel to the midline ML and that is attached to a first superior vertebra V1 by a first bone anchor 106A and to a second inferior vertebra V2 by a second bone anchor 106B. The first and second vertebrae V1, V2 can be adjacent as shown, or can be separated by one or more intervening vertebrae. The first rod 108A can extend to one or more additional vertebrae and can be secured thereto by respective bone anchors. The second portion can include a second elongate spinal rod 108B that extends substantially parallel to the midline ML and that is attached to the first superior vertebra V1 by a third bone anchor 106C and to the second inferior vertebra V2 by a fourth bone anchor 106D. The second rod 108B can extend to one or more additional vertebrae and can be secured thereto by respective bone anchors. Attachment of the bone anchors 106 and rods 108 to the patient's spine can be performed using known techniques, including open and minimally-invasive techniques.

As shown, the connector 100 can be attached in a rod-to-rod arrangement such that one end of the connector is attached to the first rod 108A and the other end of the connector is attached to the second rod 108B. Adapters 200 of the type described herein can be attached to each end of the link 102 and can then be attached to the respective first and second rods 108A, 108B. Alternatively, one or both of the adapters 200 can be attached first to the respective rod 108 and then, thereafter, to the link 102. The adapter 200 can be attached to the link 102 by coupling the mating feature 210 of the adapter to the link. For example, the threaded proximal post defined by the locking element 208 of the adapter 200 can be inserted through an opening 104 in the link 102 and through an opening in a sliding washer 114 attached to the link, and a nut 112 can be secured to the threaded post to capture the link between the body 202 of the adapter and the nut 112. Each adapter 200 can be attached to its respective rod 108 by initially placing the adapter in the unloaded configuration, snapping the adapter onto the rod to transition the adapter to the loaded but unlocked configuration, and then tightening the locking element 208 to transition the adapter to the locked configuration.

Figure 3B:
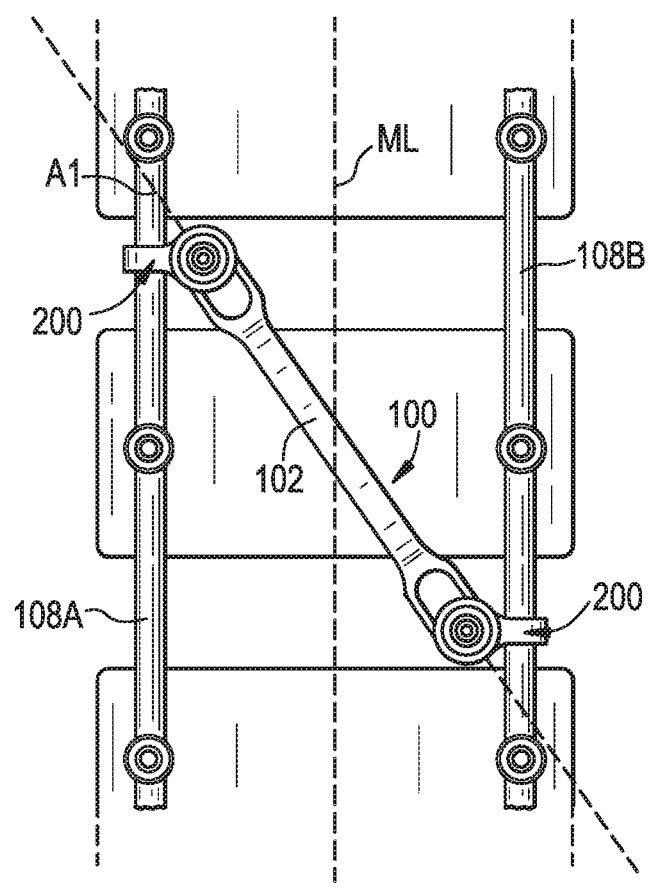
FIG. 3B is a top view of the connector and adapters of FIG. 1C attached to a spine in a diagonal rod-to-rod arrangement.

Prior to tightening the locking nuts 112, the link 102 of the connector 100 can be rotatable about the central axis A5 of the mating feature 210. Accordingly, the connector 100 can be positioned such that the central axis A1 of the link 102 extends perpendicular with respect to at least one of the first rod 108A, the second rod 108B, and the midline ML of the spine, e.g., as shown in FIG. 3A. This can allow each end of the link 102 to be attached at the same vertebral level of the spine. The connector 100 can also be positioned such that the central axis A1 of the link 102 extends diagonally or at an oblique angle with respect to at least one of the first rod 108A, the second rod 108B, and the midline ML of the spine, e.g., as shown in FIG. 3B. This can allow each end of the link 102 to be attached at a different vertebral level.

While a rod-to-rod arrangement is shown, the connector 100 can also be attached to the construct in an anchor-to-anchor arrangement of the type shown in FIG. 1A by instead attaching each end of the connector directly to a bone anchor. For example, one end of the link 102 can be attached to the first bone anchor 106A, the second bone anchor 106B, or another bone anchor in the first portion of the fixation construct and the other end of the link can be attached to the third bone anchor 106C, the fourth bone anchor 106D, or another bone anchor in the second portion of the fixation construct. Alternatively, both ends of the link 102 can be attached to bone anchors in the first portion of the fixation construct, or both ends of the link can be attached to bone anchors in the second portion of the fixation construct. In other words, the link 102 can be attached to bone anchors on the same side of the midline ML of the spine. The link 102 can be attached to the bone anchors by inserting a threaded post of the bone anchor through the opening 104 in the link and sliding washer 114 and then tightening a nut 112 on the threaded post to secure the connector 100 to the bone anchor.

The connector 100 can also be attached in a rod-to-anchor arrangement of the type shown in FIG. 1B by attaching one end of the link to a bone anchor and attaching the other end of the link to a rod using an adapter 200 of the type described herein. For example, one end of the link 102 can be attached to the first rod 108A and the other end of the link can be attached to the third bone anchor 106C, the fourth bone anchor 106D, or another bone anchor in the second portion of the fixation construct. As another example, one end of the link 102 can be attached to the first bone anchor 106A, the second bone anchor 106B, or another bone anchor in the first portion of the fixation construct, and the other end of the link can be attached to the second rod 108B. Attachment of the link 102 to the bone anchors 106 and rods 108 can be performed as described above.

Figure 4A:
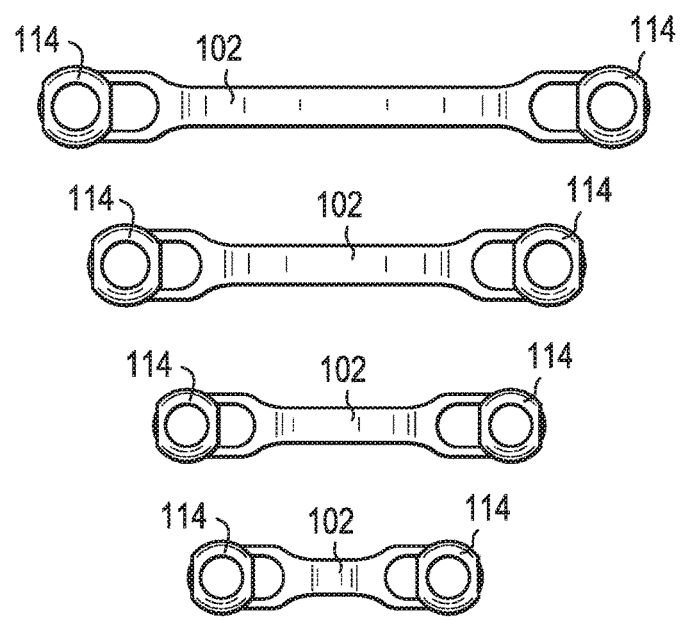
FIG. 4A is a top view of a kit of connector links having different lengths.
Figure 4B:
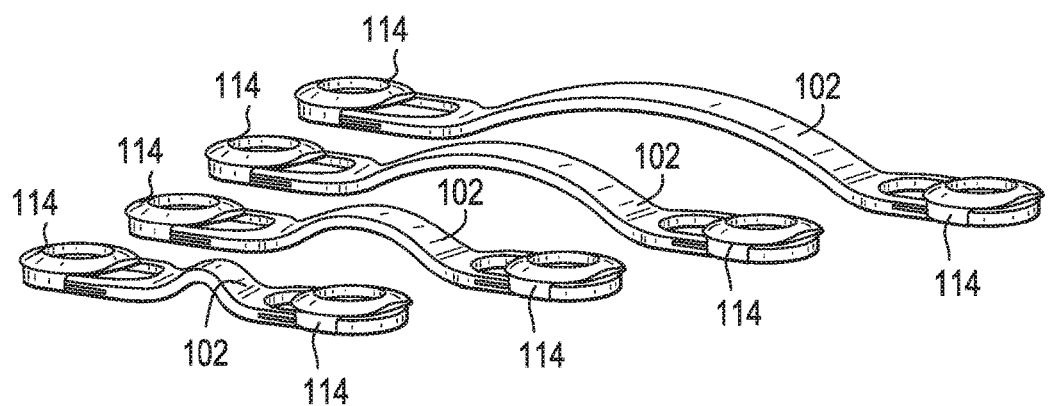
FIG. 4B is a perspective view of the kit of FIG. 4A.

One or more of the components described herein can be provided as part of a kit such that a user can select the components most appropriate for a particular surgery. An exemplary kit can include a plurality of bone anchors, a plurality of rods or other fixation elements, a plurality of adapters, and a plurality of links. The constituent members of the kit can differ from one another in various ways to provide options for the user. For example, as shown in FIGS. 4A-4B, the kit can include a plurality of links 102 each having different longitudinal lengths. The user can select the link having the length closest to the span between first and second portions of the fixation construct, making any fine adjustments that may be needed using the sliding washers 114. The kit can include a plurality of rods each having a different length or each having a different diameter. The kit can include a plurality of adapters, each configured to snap onto and drag against rods of different diameters or of different cross-sectional shapes.

While a posterior fixation construct is shown, the connectors and adapters described herein can be used with anterior fixation constructs, lateral fixation constructs, or any combination of the three. While a procedure is shown with respect to a human spine, the connectors and adapters herein can be used with procedures on any bone, bones, or other structures in any living or non-living subject (e.g., humans, animals, machines, etc.). The connectors and adapters can be implanted within the patient, e.g., as part of an implanted fixation construct, or can be partially or completely external to the patient, e.g., as part of an external fixation construct. The connectors and adapters can be attached to the construct during the same procedure in which the construct is attached to the patient. Alternatively, the connectors and adapters can be added to a previously-installed construct in a subsequent revision procedure. While pedicle or lateral mass screws and fixation rods are shown, it will be appreciated that various other hardware can be employed, such as bone hooks, wires, tethers, etc. The connectors and adapters can be used in the cervical region of the spine, in the thoracic region of the spine, in the lumbar region of the spine, in the sacral region of the spine, or in any combination of the above regions. The connectors and adapters can be installed in minimally-invasive surgical procedures, in open surgical procedures, or in hybrid procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

Adapters of the type described herein can advantageously allow a single connector link to be used interchangeably for rod-to-rod connections, rod-to-anchor connections, and anchor-to-anchor connections, thus improving the modularity of such components. Adapters of the type herein can provide a low profile rod attachment structure, which can advantageously facilitate use in tight spaces such as between bone anchors implanted in adjacent levels of the spine, including in the cervical spine or at the cervicothoracic junction. Adapters of the type described herein can include snap and drag features which can advantageously provide tactile or audible feedback to confirm securement to the rod and provide provisional retention and positioning until final tightening is performed. Adapters of the type described herein can allow for one or more degrees of freedom between the clamping arm and the body and/or can include a rod channel with a varying geometry, which can advantageously facilitate use with various sized rods or ease installation of the connector.

The connectors and adapters disclosed herein can be constructed from any of a variety of known materials. Exemplary materials include those which are suitable for use in surgical applications, including metals such as nickel, titanium, cobalt chromium, and stainless steel, polymers such as PEEK, ceramics, carbon fiber, and so forth. The various components of the connectors and adapters disclosed herein can be rigid or flexible. One or more components or portions of the connectors and adapters can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. An implant adapter, comprising:
a body having proximal and distal ends that define a body axis extending therebetween, the body including a rod-receiving channel and an opening;
a locking element received through the opening of the body;
a clamping arm coupled to the locking element; and
a bias element that biases the clamping arm towards the channel of the body;
wherein the adapter has a locked configuration in which the clamping arm is configured to clamp a rod against the channel of the body to prevent movement between the rod and the adapter; and
wherein the adapter has an unlocked configuration in which the clamping arm can independently: (1) translate axially relative to the body along the body axis, (2) translate laterally relative to the body in a direction perpendicular to the body axis, and (3) rotate relative to the body about an axis perpendicular to the body axis.

2. The adapter of claim 1, wherein the clamping arm is constrained from rotating relative to the body about the body axis and any axis parallel to the body axis in both the locked and unlocked configurations.

3. The adapter of claim 2, wherein one of the body and the clamping arm includes a male key that is received within a female keyway formed in the other of the body and the clamping arm.

4. The adapter of claim 1, wherein the channel is formed in a hook projecting radially outward from the body, the hook having a height parallel to a rod axis of the channel that is less than half a diameter of the channel.

5. The adapter of claim 1, wherein the channel has a radius of curvature that varies along the perimeter of the channel.

6. The adapter of claim 1, wherein the opening of the body is enlarged relative to a portion of the locking element received therein.

7. The adapter of claim 6, wherein the opening is cylindrical and has a diameter greater than a diameter of a corresponding cylindrical portion of the locking element received within the opening.

8. The adapter of claim 6, wherein the opening is elongated and includes a major dimension that is greater than a diameter of a corresponding cylindrical portion of the locking element received within the opening and a minor dimension that is substantially equal to the diameter of the corresponding cylindrical portion of the locking element.

9. The adapter of claim 8, wherein the major dimension is perpendicular to a rod axis of the channel and perpendicular to the body axis.

10. The adapter of claim 1, wherein the locking element comprises a screw that is threaded into a threaded recess formed in the clamping arm.

11. The adapter of claim 1, wherein the locking element includes a shoulder projecting radially outward therefrom.

12. The adapter of claim 11, wherein the bias element is disposed between the body and the shoulder of the locking element.

13. The adapter of claim 12, wherein the bias element comprises a wave spring.

14. The adapter of claim 12, wherein the bias element comprises a compression spring, a Belleville washer, or a washer with tabs.

15. The adapter of claim 11, wherein the shoulder defines a spherical distal-facing surface positioned opposite to a spherical proximal-facing surface of the body.

16. The adapter of claim 1, wherein the locking element includes a mating feature configured to attach the adapter to a link of a connector.

17. The adapter of claim 16, wherein the mating feature comprises a proximal head of the locking element having an externally-threaded surface.

18. The adapter of claim 1, wherein the clamping arm and the body define an aperture therebetween through which a rod can be passed to insert the rod into the channel of the body.

19. The adapter of claim 18, wherein the aperture is configured to expand as a rod is passed therethrough and to contract once the rod is positioned in the channel such that the adapter, in the unlocked configuration, is configured to snap onto and retain the rod within the channel.

20. The adapter of claim 1, wherein, in the unlocked configuration, the bias element urges the clamping arm against a rod received in the channel to apply a drag force to the rod.

21. The adapter of claim 1, wherein the bias element is disposed between the clamping arm and a head of the locking element.

22. The adapter of claim 1, wherein the clamping arm is threadably coupled to the locking element.

23. An implant adapter, comprising:
  a body having proximal and distal ends that define a body axis extending therebetween, the body including a rod-receiving channel and an opening;
  a locking element received through the opening of the body;
  a clamping arm coupled to the locking element; and
  a bias element that biases the clamping arm towards the channel of the body;
  wherein the adapter has a locked configuration in which the clamping arm is configured to clamp a rod against the channel of the body to prevent movement between the rod and the adapter; and
  wherein the adapter has an unlocked configuration in which the locking element can independently: (1) translate axially relative to the body along the body axis, (2) translate laterally relative to the body in a direction perpendicular to the body axis, (3) rotate relative to the body about an axis perpendicular to the body axis, and (4) rotate relative to the body about the body axis.

24. The adapter of claim 23, wherein the bias element is disposed between the clamping arm and a head of the locking element.

25. The adapter of claim 23, wherein the clamping arm is threadably coupled to the locking element.

26. An implant adapter, comprising:
  a body having proximal and distal ends that define a body axis extending therebetween, the body including a rod-receiving channel and an opening;
  a locking element received through the opening of the body;
  a clamping arm threadably coupled to the locking element; and
  a bias element that biases the clamping arm towards the channel of the body;
  wherein the adapter has a locked configuration in which the clamping arm is configured to clamp a rod against the channel of the body to prevent movement between the rod and the adapter; and
  wherein the adapter has an unlocked configuration in which the clamping arm can: (1) translate axially relative to the body along the body axis, (2) translate laterally relative to the body in a direction perpendicular to the body axis, and (3) rotate relative to the body about an axis perpendicular to the body axis.

27. The adapter of claim 26, wherein the locking element comprises a screw that is threaded into a threaded recess formed in the clamping arm.

28. The adapter of claim 26, wherein the locking element includes a shoulder projecting radially outward therefrom.

29. The adapter of claim 28, wherein the bias element is disposed between the body and the shoulder of the locking element.

30. The adapter of claim 26, wherein the locking element includes a mating feature configured to attach the adapter to a link of a connector.

31. The adapter of claim 30, wherein the mating feature comprises a proximal head of the locking element having an externally-threaded surface.

* * * * *